United States Patent [19]
Eadington et al.

[11] Patent Number: 5,543,616
[45] Date of Patent: Aug. 6, 1996

[54] IDENTIFYING OIL WELL SITES

[75] Inventors: Peter J. Eadington, East Ryde; Mark Lisk; Francis W. Krieger, both of North Ryde, all of Australia

[73] Assignee: Commonwealth Scientific Industrial Research Organisation, Australia

[21] Appl. No.: 506,181

[22] Filed: Jul. 25, 1995

[51] Int. Cl.$^6$ .................................................. G01N 33/24
[52] U.S. Cl. ............................................. 250/55; 250/301
[58] Field of Search .................................. 250/255, 301, 250/461.1; 166/252.2; 73/153

[56] References Cited

U.S. PATENT DOCUMENTS 5,241,859  9/1993  Smith ...................................... 250/301

OTHER PUBLICATIONS

Lisk and Eadington, "Oil Migration in the Cartier Trough, Vulcan Sub-basin", Commonwealth Scientific and Industrial Research Organisation, Australia, Aug., 1994, pp. 301–312.

*Primary Examiner*—Davis L. Willis
*Assistant Examiner*—Kiet T. Nguyen
*Attorney, Agent, or Firm*—Ladas & Parry

[57] ABSTRACT

Methods for determining maximum oil saturation and possible oil zone location use natural oil inclusions in rock grains of granular rock samples. A first technique involves quantitatively determining the total number of grains in the sample and, of those grains, the number that include oil within them, thereby yielding a ratio (GOI); and correlating that ratio against standard rock samples to yield the maximum oil saturation. A second technique involves determining the location of oil containing and/or oil absent zones in geological sites by (a) sampling in the geological site from a first rock portion capable of granular retention of oil and subjecting the first rock portion sample to the technique of GOI; (b) sampling in the geological site from one or more further and distinct rock portions, each capable of granular oil retention, and subjecting the or each further rock portion sample to the technique of GOI; and (c) comparing the results of GOI between the first rock portion and one or more of each further rock portion to determine whether or not the or each further rock portion is located in a different zone within the geological site from that of the first rock portion.

9 Claims, 3 Drawing Sheets

IDENTIFYING OIL WELL SITES

FIELD OF THE INVENTION

The present invention relates to methods and techniques for identifying oil well sites (defined herein) through the determination of the maximum oil saturation in a granular rock sample, for example, in a suspected oil well site. The invention also allows the determination of the location of various zones in a site, including zones that have never retained oil, zones that have previously retained oil or zones that currently retain oil. The invention will be described primarily with reference to its use with sandstone based oil reservoirs, but it should be appreciated that the invention can find application with other types of granular rock reservoirs, including carbonate-type rock reservoirs. The invention has particular application with test drilling and exploration for oil well sites, but can also be used during site commercial drilling and for re-exploration.

BACKGROUND ART

In exploration for oil well sites, for example offshore (subsea) well sites, when a potential well site has been identified, (ie. using standard geological exploration techniques), it is usual practice to test-drill the site to ascertain whether the site contains oil (or could contain oil other than at the point of drilling).

Test drilling is typically expensive and is performed by stringing together pieces of pipe and drilling through, usually, a shale crust until a reservoir (e.g. of sandstone) suspected of containing oil is reached. The rate of penetration of drilling increases when a sandstone reservoir is reached, and this signifies that testing for oil in the reservoir can shortly commence. Mud and cuttings from the drilling operation eventually reach the surface (e.g. in offshore exploration) and these are analysed in order to determine the presence or absence of oil. The techniques of cuttings analyses are collectively referred to as "shows". Known show techniques include detecting hydrocarbon gases in the mud by flame ionisation or thermal conductivity, detecting oil fluorescence by ultraviolet illumination of the mud, and oil stain, oil odour and oil cutting (adding of solvent) techniques etc. However, the existing techniques are qualitative and can be subject to false and/or ambiguous results. For example, heavy mud used to seal around the drill string during drilling may include hydrocarbon and this can also reach the surface during testing giving false results.

It would be advantageous if a show technique could be provided that quantitatively indicates oil presence (or absence in a reservoir), for example during test-drilling and/or drill site re-exploration.

SUMMARY OF INVENTION

In a first aspect the present invention provides a method of using natural oil inclusions in rock grains to determine the maximum oil saturation that a granular rock sample has had, comprising the steps of:

quantitatively determining the total number of grains in the sample and, of those grains, the number that include oil within them, thereby yielding a ratio; and correlating that ratio against standard rock samples (as herebelow defined) to yield the maximum oil saturation.

The ratio of the number of grains in a sample that include oil within them (e.g. NGO) to the total number of grains in the sample (e.g. TGN) can be expressed as a percentage and this will hereinafter be referred to as "GOI" (ie. Grains containing Oil Inclusions). The percentage value of GOI is calculated in a sample by expressing the ratio of the number of grains with oil therein to the total number of grains as a percentage.

The calculated GOI ratio for a given sample can be collated against standard rock samples to yield maximum oil saturation for the given sample (e.g. for a sample from a suspected oil well site).

The term "standard rock samples" refers to rock samples of predetermined oil saturation (and thus known GOI ratios). This predetermined oil saturation can, for example, be calculated by a laborious technique such as grinding or breaking down grains in a given sample to liberate the oil therewithin. The actual amount of liberated oil can then be measured using appropriate sensitive and accurate quantitative techniques and this can be correlated against actual oil quantities extracted from a site.

The method of the first aspect can therefore be used as a quantitative "show". The method recognises that during the crystallisation of minerals such as quartz, feldspar and calcite in a site that already has oil present therein, oil can be included within many resulting crystals (ie. during diagenesis in the site).

When the terminology "oil well site(s)" is used in the present specification, it is intended to include any site in which diagenetic oil inclusion could have occurred, and thus includes sites where test-drilling will be performed, should have been performed, or may need to be re-performed, and those which are under current oil production.

Preferably the technique of GOI involves taking a rock sample (e.g. such as a rotary core, side wall core or ditch cutting sample) from a drill site, preparing a thin section from this sample and then placing the thin section in a fluorescence microscope. The thin sample can then be subjected to radiation e.g. using ultraviolet radiation of wavelengths of about 365 nm and/or violet radiation of wavelengths of about 410 nm, which induce oil fluorescence (and produce visible emission spectra when the aromatic fraction of the oil fluoresces). Thus, any grains having oil inclusions therewithin can be viewed and counted, and also the total number of grains can be counted to yield a GOI value.

In a second aspect the present invention provides a method for determining the location of oil containing and/or oil absent zones (as herebelow defined) in geological sites comprising the steps of:

(a) sampling in the geological site from a first rock portion capable of granular retention of oil and subjecting the first rock portion sample to the technique of GOI;

(b) sampling in the geological site from one or more further and distinct rock portions, each capable of granular oil retention, and subjecting the or each further rock portion sample to the technique of GOI; and (c) comparing the results of GOI between the first rock portion and one or more of each further rock portion to determine whether or not the or each further rock portion is located in a different zone within the geological site from that of the first rock portion.

When the terminology "oil containing and/or oil absent zones" is employed, it refers to geological rocks that are capable of retaining oil within individual grains and that also function as oil accumulation zones, and includes zones which:

(a) have never had oil retained therein;

(b) have had oil retained therein at some point in time, but no longer retain significant and/or economical quantities of oil therein; and (c) presently retain oil therein.

In some sandstone oil reservoirs there is no significant or detectable oil present in the pores of the sandstone. However, prior to the methods of the first and second aspects there was no quantitatively reliable way of establishing whether the area may have previously been an oil reservoir (and thus adjacent to a reservoir which might be an actual and/or commercially significant oil reservoir). Areas which may have previously been an oil reservoir are hereinafter referred to as "residual (GOI) zone(s)". By identifying a reservoir as a residual (GOI) zone, incentive may be provided for further exploration or re-exploration of an oil well site (e.g. by drilling or re-drilling at adjacent lateral and/or deeper or shallower sites) which may ultimately yield commercial quantities of oil. The method of the second aspect also enables a palaeo fluid contact (ie. the boundary between different phases in a reservoir such as oil-water or gas-oil phases) to be identified, and thus the method may ultimately lead to the location of oil adjacent to a particular region, where previous tests would have failed to identify that the adjacent oil zone(s) might have been present. Thus, by comparing the results of GOI between one rock portion and another rock portion, it may be possible to establish whether or not a zone is a residual (GOI) zone.

Once again, in the second aspect it is preferred that the geological site is an oil well site (as defined above) and sampling is performed by obtaining a cutting and/or a core during drilling. In this regard, it is preferred that the cutting and/or core is retrieved from:

(a) a sandstone based rock; or (b) a carbonate based rock.

The incentive for further drilling may also be provided when a GOI value of about 5% or greater is calculated to establish a zone as:

(i) having had oil therein; or (ii) presently having oil therein, whereas when a GOI value of about 1% or less is calculated, a zone that never has had oil therein may be established.

BRIEF DESCRIPTION OF THE DRAWINGS

Notwithstanding any other forms which may fall within the scope of the present invention, preferred embodiments of the invention will now be described, by way of example only, with reference to examples below which refer to the accompanying drawings in which.

MODES FOR CARRYING OUT THE INVENTION

Figure 1:
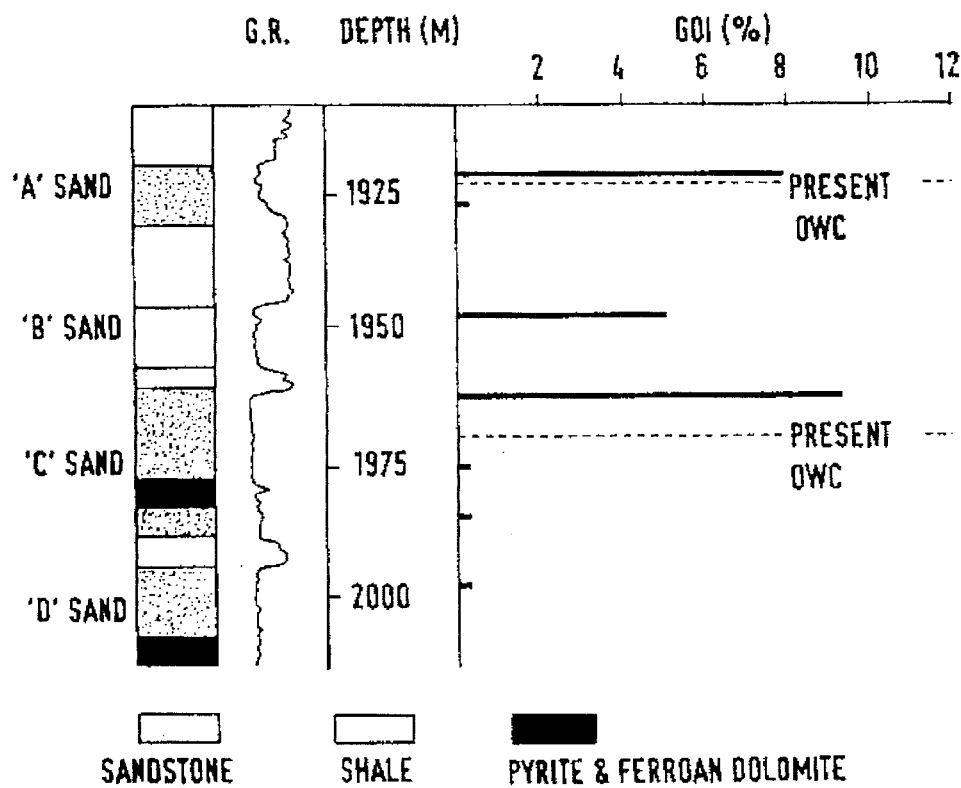
FIG. 1 shows the location of various rock samples and the GOI results for an oilfield in the Dampier Basin, Western Australia.

Preferred techniques of GOI were used to determine both the presence or absence of oil within particular zones and the location of boundaries between particular zones. The techniques were found to be useful in establishing the location of residual zones, (which subsequently could lead to the location of an oil zone).

It was generally determined that samples from existing oil-producing and residual zones had GOI values between 5% and 70%. GOI as a percentage was established according to the following equation:

$$GOI(\%) = NGO/TGN \times 100/1 (\%)$$

where GOI=grains containing oil inclusions, NGO=the number of grains with oil included therein and TGN=the total number of grains in a sample.

It was also determined that 5% was a threshhold GOI value in recognising both oil zones and residual (GOI) zones, and that zones which had never contained or had an accumulation of oil (eg. subsea rock formations permeated by water) had GOI values less than 1%.

The technique was observed to be useful in establishing the location of palaeo fluid contacts such as oil-water contact boundaries, gas-oil contact boundaries etc. These contacts were established when measuring GOI values at different intervals in a borehole formed during test and commercial drilling, and observing where in the borehole the GOI value decreased from a high value (ie. greater than 5%) to a low value (ie. less than 1%). In general, the information derived from GOI analyses was found to be very useful information in all types of oil exploration and drilling.

Preferred GOI Methods

Samples of reservoir rock from various Australian offshore test drill sites (ie. resulting from the test drilling operation) were retrieved. Satisfactory samples included rotary core, cuttings such as ditch cuttings, side wall core and rotary side wall core samples.

The samples were then cut, ground and polished to produce a thin section (usually 0.08 mm) for mounting on a glass slide and so as to present a polished upper surface with no cover glass. Core samples were impregnated with epoxy prior to preparation, whereas cutting samples were dispersed in epoxy prior to preparation.

Typically, the glass slides were then mounted in a fluorescence microscope capable of irradiating both UV and violet light. Where the samples were from a sandstone reservoir, sand grains were typically observed to be 0.05 to 1 mm in diameter. The technique of dark field fluorescence microscopy was employed. In this method, the oil filled fluid inclusions were revealed by excitation with ultraviolet light of about 365 nm and violet light of about 410 nm (ie. typically light of less than 4000 Angstrom) and then the fluorescent light resulting from excitation of the aromatic fractions of the oil was observed through a filter at wavelengths greater than about 4200 Angstrom (ie. emission spectra ranging from yellow (about 550 nm) to blue (about 440 nm)).

An autoscan microscope stage was then used to position the sample on the microscope by robotic motor action under computer control. The sample was examined with a 10×objective lens and a square 10×10 grid in the ocular lens that overlay an area of (0.0625 mm×0.0625 mm) on the sample. A sample on a glass slide lens had an area of about (20×30) mm² which enabled the positioning of, usually, a 1400 grid overlay thereover (ie. having 1400 positions, or hereinafter "fields") for complete inspection. Collectively, the contiguous fields formed a rectangular area that covered as much of the thin section as possible, and all of this area could be examined by moving the sample in traverses by a step distance equal to the size of the grid in the ocular lens.

A limited sample of fields (eg. 100) was selected for counting from the possible 1400 fields, this sample being made at random using the computer commanding the autoscan positioner. Sample irradiation was then commenced. Using the square grid in the ocular lens of the microscope as a guide, the total number of grains were counted as were the number of grains containing oil inclusions in each selected field.

An unbiased estimate of the total number of grains in a sample was obtained by counting whole grains that lay within the grid or that crossed two adjacent edges of the grid or the corner therebetween. Grains that crossed the other two edges or the three associated corners of the grid were not counted. [This method avoided bias due to grains crossing the edge of the grid and avoided potential errors that might arise in estimating fractions of grains across the edge of the grid or double counting if whole grains across all four edges of the grid were counted].

In the technique, the sample appeared generally dark, and bright lights appeared where there was fluorescence. GOI was then computed as the number of grains containing oil inclusions summed for the 100 fields as a percentage of the total number of grains also summed for the 100 fields.

The identification and interpretation of residual oil zones was also possible in situ (ie. whilst drilling) when the GOI values were directly turned into a graph on a geophysical, electric or lithologic log of the borehole.

STATISTICAL VALIDITY

To check the statistical validity of the GOI testing, two methods were used to obtain a statistically meaningful GOI determination.

Method (1)

Samples with a high proportion of grains containing oil inclusions, which typically had GOI values greater than 5%, were counted at a number of fields selected at random from the total number of field locations. Typically in testing there were 1000–1500 fields and at each field the total number of grains and the total number of grains containing oil inclusions were counted. As indicated above, the GOI was usefully calculated from the aggregate counts for 100 fields.

Figure 2:
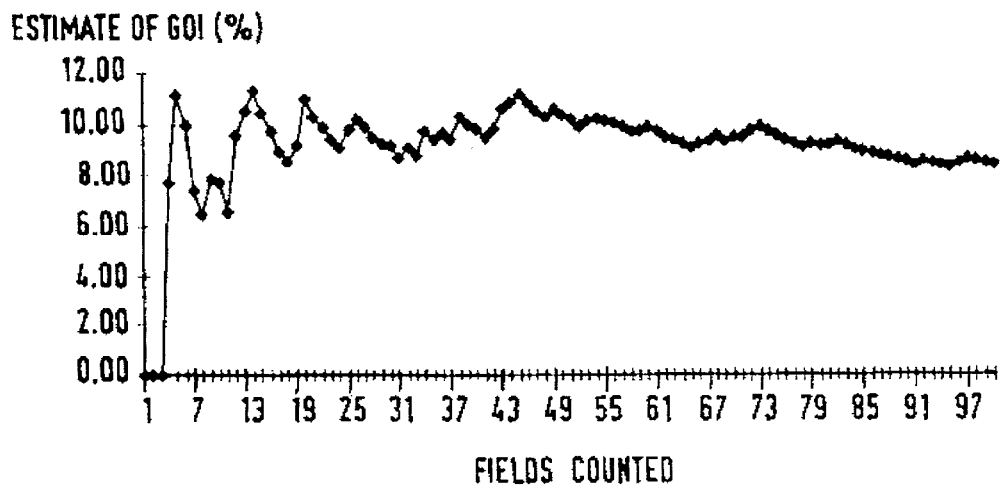
FIG. 2 shows a plot of progressive GOI values indicating how sampling error can be reduced when a preferred method (1) of establishing GOI (below) is followed.

The statistical validity of the method was checked by plotting a graph of the aggregate GOI for the 100 fields in a progressive manner. The results of this graph are shown in FIG. 2. Progressive GOI values were found to fluctuate within limits that decreased from±78% with less than 35 fields counted to ±11% when more than 75 fields were counted.

Method (2)

Samples with a low proportion of grains containing oil inclusions, which typically had GOI values less than 5%, were counted by observing every field on the thin section to obtain the total number of grains containing oil filled fluid inclusions.

An estimate of the total number of grains in the section was made by counting the number of grains at 35 randomly selected fields and multiplying the average number of grains per field by the total number of fields on the sample. GOI was then calculated as the ratio of the total number of grains containing oil filled fluid inclusions divided by the estimate of the total number of grains.

Figure 3:
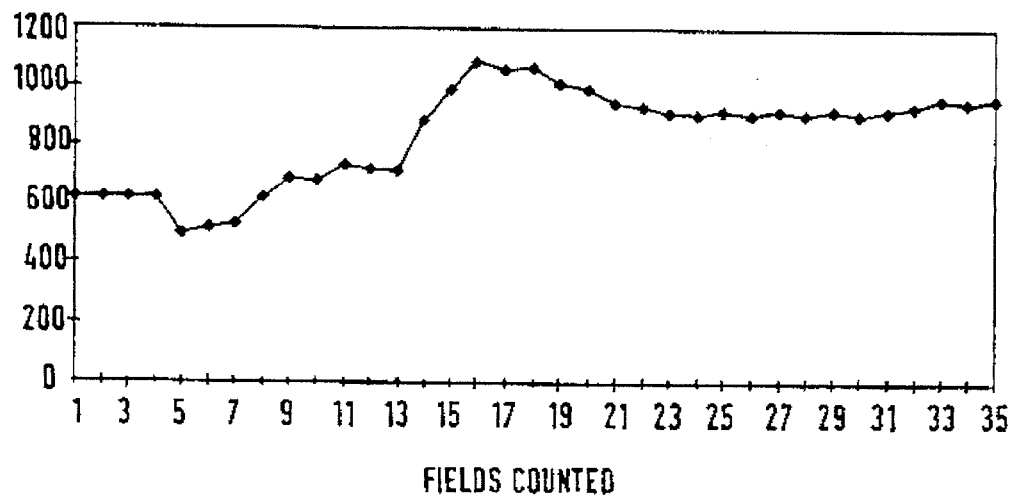
FIG. 3 shows a plot of the progressive estimates of the total number of grains in a thin section sample and how error can be reduced when a preferred method (2) of calculating GOI (below) is followed.

The statistical validity of the estimate of the total number of grains was checked by plotting the progressive estimate of the number of grains for the 35 random fields. The results of this plot are shown in FIG. 3. The progressive estimate was found to fluctuate within limits that decreased from ±48% for less than 20 fields to ±4% for more than 25 fields.

EXAMPLES

Example 1

Preferred Calculation of GOI in the Talisman 1 Oilfield, Dampier Basin, Western Australia Samples of drill cuttings from two oil columns in the Talisman 1 reservoir, one above the other, were counted. The upper oil column was contained within the A sand (see FIG. 1) and there was determined to be an oil-water contact at 1923.5 m below the rotary table (mrt). A lower oil column was found to be contained within B and C sands (FIG. 1) and an oil-water contact was located at 1971.5 mrt.

The results of GOI were then presented in Table 1 (below). The oil zone sample from the upper oil column was found to have a GOI of 8.4% and the water zone sample from below the oil-water contact was found to have a GOI of 0.2%. Two oil zone samples from the lower oil column were found to have GOI values of 5% and 9.4% respectively and three water zone samples from below the oil-water contact were found to have GOI values of 0.3%, 0.7% and 0.9% respectively.

TABLE 1

| GOI Results in the Talisman 1 Oilfield | | | | |
|---|---|---|---|---|
| Depth (m kb) | Formation | GOI (%) | Total Grains Counted | Total Grains with Oil incls |
| 1915–20 | 'A' sand oil zone | 8.4 | 451 | 38 |
| 1925–30 | 'A' sand water zone | 0.2 | 958 | 2 |
| 1945–50 | 'B' sand oil zone | 5.0 | 261 | 13 |
| 1959–62 | 'C' sand oil zone | 9.4 | 330 | 31 |
| 1974–77 | 'C' sand water | 0.9 | 2498 | 23 |
| 1986–89 | 'C' sand water | 0.7 | 2826 | 20 |
| 1995–98 | 'D' sand water | 0.3 | 2042 | 6 |

It can be seen that the difference in GOI values between samples from oil saturated rocks and samples with no oil saturation differed by approximately one order of magnitude. That is to say values ranging from about 5% to 10% in the oil zone were found whereas values ranging from about 0.3% to 1% in the water zone were found.

FIG. 1 graphically presents the results of GOI analysis in the Talisman 1 Oilfield. FIG. 1 also includes a lithology log (column 1), a gamma ray log (column 2), and designated G.R., and a depth scale (column 3) to show the various depths of the different zones within the geological sites. GOI values are shown as horizontal bars on a scale from 0% to 12% at the depth from which the samples were derived. The permeable reservoir rocks were revealed on the gamma ray trace as intervals of relatively low gamma ray count and were represented as a stippled pattern on the lithology log.

The intervening shale seal rocks were intervals with relatively high gamma ray count and were shown without pattern on the lithology log. The current contacts between oil and water were shown as dashed horizontal lines.

Example 2

GOI Portfolio of Various Australian Oilfields.

Figure 4:
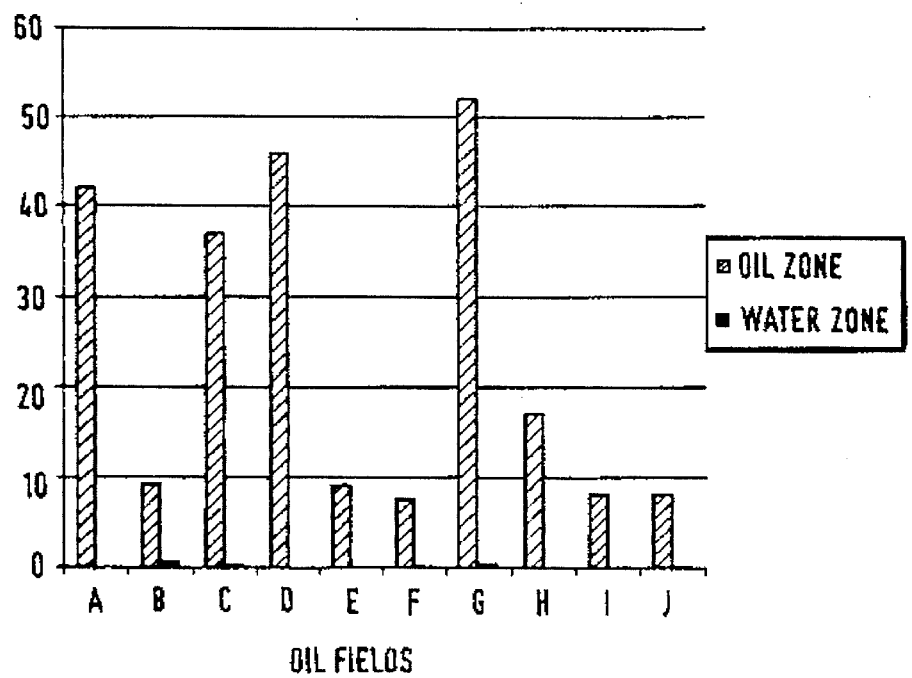
FIG. 4 plots the results of a preferred GOI test in ten different subsea oilfields located off the north-west shelf of Australia.

GOI was measured in ten oilfields in the north-west shelf of Australia. Samples from the oilfields included potentially oil-containing sandstone reservoir rocks. The ten fields were designated as A through to J and the results were presented in Table 2 and graphically in FIG. 4.

Samples from the oil zones were found to have GOI values from 9% to 52%. Samples from the water zone below the oil accumulations were found to have GOI values from 0% to 0.7%.

Some of those zones were observed as having a residual (GOI) zone below with an elevated GOI indicating that the reservoir had been filled with oil to the base of the reservoir rock. In such cases, a palaeo oil-water contact could not be delineated and so the annotation "residual" was deemed to be appropriate (see Table 2).

TABLE 2

GOI Values from Oil Zone and Water Zone

|  | Oil Zone | Water Zone |
| --- | --- | --- |
| Field A | 42 | Residual |
| Field B | 9.4 | 0.7 |
| Field C | 37 | 0.3 |
| Field D | 46.0 | Residual |
| Field E | 9.1 | Residual |
| Field F | 7.7 | 0.2 |
| Field G | 52.0 | 0.5 |
| Field H | 17.0 | 0.0 |
| Field I | 8.2 | Residual |
| Field J | 8.2 | 0.2 |

Figure 5:
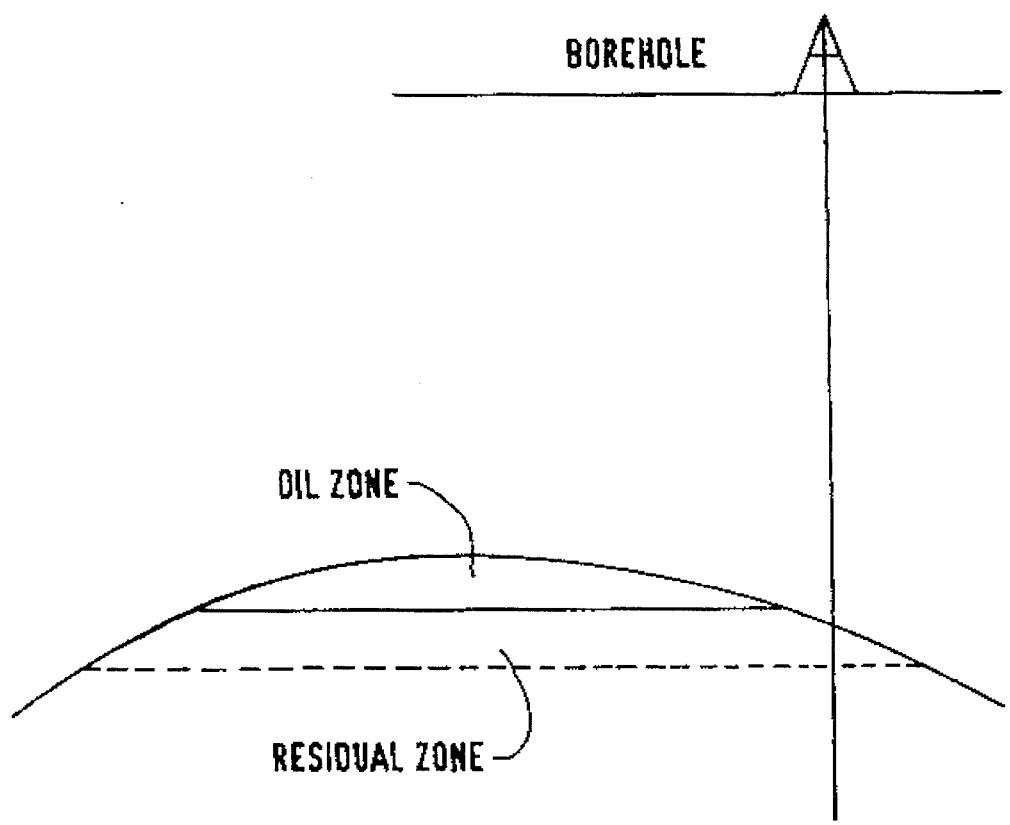
FIG. 5 shows a schematic illustration in cross-section of a potential oil well site showing how a drilling operation (borehole) can locate a residual (GOI) zone only, when an oil zone is in close proximity.

Referring to the schematic representation of FIG. 5 it can be seen how a residual (GOI) zone may underlie an oil zone and how the oil zone may be missed if the borehole is drilled at an inappropriate place and ambiguous or negative "show" test results are received. GOI can be used to identify the residual (GOI) zone so that a now water wet zone might indicate that there is an oil accumulation somewhere above this zone (e.g. where the oil accumulation has decreased in size through leakage etc). Alternatively, GOI with other testing may identify a residual zone with a gas column, indicating that oil may have been displaced downwardly and may now reside as an oil column beneath the gas.

FINDINGS

It was found that there was a significant difference in GOI between oil zone samples and water zone samples. The difference was found to be approximately one order of magnitude. GOI was also found to be high in residual (GOI) zones (typically rocks that once had a high oil saturation but were now water wet due to loss of oil). The accuracy in the discovery of oil zones (including residual (GOI) zones) was attributable to the technique of GOI, because GOI counting was always made on grains containing oil inclusions which, once formed, were known to be permanent records of the rock that previously had a high oil saturation.

From this it was determined that GOI can be reliably used in oil exploration to determine whether a rock has had an oil accumulation at some stage or has never had an oil accumulation and also can be used as an adjunct to current procedures for testing for the presence of oil accumulation. GOI can also be used to identify rocks that have not had high oil saturation, to screen rocks prior to testing (e.g. prior to an expensive drill stem test) and by identifying and removing from contention those rocks that have never had an oil accumulation. Also, by knowing that rocks once contained oil provides information that ambiguous results from other forms of testing for oil are to be questioned, and that repeat testing or supplementation with alternative tests to obtain a definitive result should ensue.

The techniques were found to be particularly applicable to subsea sandstone reservoirs, but could also be applicable to subterranean (ie. underground reservoirs on land), and to other types of granular rocks (e.g. carbonate rocks such as dolomites).

Whilst the invention has been described with reference to a number of preferred embodiments it should be appreciated that the invention can be embodied in many other forms.

We claim:

1. A method of using natural oil inclusions in rock grains to determine the maximum oil saturation that a granular rock sample has had, comprising the steps of:

quantitatively determining the total number of grains in the sample and, of those grains, the number that include oil within them, thereby yielding a ratio; and correlating that ratio against standard rock samples to yield the maximum oil saturation.

2. A method as claimed in claim 1, wherein the rock sample is a thin section of a larger rock cutting and/or core from an oil well site and the step of quantitatively determining the total grain number (TGN) and number of grains with oil therewithin (NGO) involves placing the thin section in a fluorescence microscope, irradiating the sample with electromagnetic radiation of wavelengths to cause fluorescence of aromatic fractions of the oil within any grains containing the oil inclusions and then counting each of NGO and TGN to yield a ratio of the grains containing oil inclusions.

3. A method as claimed in claim 2, wherein the wavelengths include ultraviolet wavelengths of about 365 nm, and/or violet wavelengths of about 410 nm.

4. A method as claimed in claim 2, wherein the larger rock cutting is retrieved from either a subsea or subterranean oil well site.

5. A method as claimed in claim 1, wherein the rock sample is retrieved from:

(a) a sandstone based rock; or (b) a carbonate based rock.

6. A method for determining the location of oil containing oil absent zones in geological sites comprising the steps of:

(a) sampling in the geological site from a first rock portion capable of granular retention of oil and subjecting the first rock portion sample to the technique of GOI;

(b) sampling in the geological site from one or more further distinct rock portions, each capable of granular oil retention, and subjecting each further rock portion sample to the technique of GOI; and (c) comparing the results of GOI between the first rock portion and one or more of each further rock portion to determine whether or not the further rock portion is located in a different zone within the geological site from that of the first rock portion.

7. A method as claimed in claim 6, wherein the geological site is either a subsea or subterranean oil well site and the sampling is performed by obtaining a thin section of a larger rock cutting and/or a core during drilling of the site.

8. A method as claimed in claim 7, wherein the larger rock cutting and/or core is retrieved from:
 (a) a sandstone based rock; or
 (b) a carbonate based rock.

9. A method as claimed in claim 6 wherein, when a GOI value of about 5% or greater is calculated, a zone:
 (i) having had oil therein; or
 (ii) presently having oil therein; is established;

whereas when a GOI value of about 1% or less is calculated, a zone that has never had oil therein is established.

* * * * *